(12) United States Patent
Yagi (10) Patent No.: US 7,248,928 B2
(45) Date of Patent: Jul. 24, 2007

(54) ARTIFICIAL EYE SYSTEM

(75) Inventor: Toru Yagi, Nagoya (JP)

(73) Assignee: Nidek Co., Ltd., Gamagori-Shi (JP)

( * ) Notice: Subject to any disclaimer, the term of this patent is extended or adjusted under 35 U.S.C. 154(b) by 465 days.

(21) Appl. No.: 10/471,095

(22) PCT Filed: Mar. 27, 2002

(86) PCT No.: PCT/JP02/03027

§ 371 (c)(1),
(2), (4) Date: Sep. 8, 2003

(87) PCT Pub. No.: WO02/080828

PCT Pub. Date: Oct. 17, 2002

(65) Prior Publication Data

US 2004/0102843 A1 May 27, 2004

(30) Foreign Application Priority Data

Mar. 30, 2001 (JP) ............................ 2001-101484

(51) Int. Cl.
*A61N 1/18* (2006.01)
(52) U.S. Cl. ..................... 607/54; 607/53; 607/61; 607/139; 607/141; 623/4.1; 623/6.63
(58) Field of Classification Search ............ 607/53–54, 607/116, 61, 141, 139; 623/6.63, 4.1
See application file for complete search history.

(56) References Cited

U.S. PATENT DOCUMENTS

| | | | |
|---|---|---|---|
| 4,784,161 A * | 11/1988 | Skalsky et al. ............. | 607/116 |
| 5,037,376 A | 8/1991 | Richmond et al. | |
| 5,106,179 A | 4/1992 | Kamaya et al. | |
| 5,397,350 A | 3/1995 | Chow et al. | |
| 5,683,443 A | 11/1997 | Munshi et al. | |
| 5,895,415 A * | 4/1999 | Chow et al. .................. | 607/54 |
| 5,897,583 A | 4/1999 | Meyer et al. | |
| 6,032,062 A | 2/2000 | Nisch | |
| 2002/0095193 A1* | 7/2002 | Ok et al. ...................... | 607/54 |

FOREIGN PATENT DOCUMENTS

| | | |
|---|---|---|
| GB | 1 553 969 | 10/1979 |
| JP | U 1-93930 | 6/1989 |
| JP | A 10-258129 | 9/1998 |
| WO | WO 96/39221 | 12/1996 |
| WO | WO 99/45870 | 9/1999 |

* cited by examiner

*Primary Examiner*—Carl Layno
*Assistant Examiner*—Deborah Malamud
(74) *Attorney, Agent, or Firm*—Oliff & Berridge, PLC (57) ABSTRACT

An artificial eye system may include an extracorporeal unit mounted outside a user's body and an intracorporeal unit 3 mounted inside a user's eye. The extracorporeal unit 2 may include a visor and a power supply unit. The visor may include a primary coil, an image receiving element that receives a picture image, a light emitting element that transmits an electric stimulus signal produced based on an image signal from the image receiving element, and an eye-gaze point recognizing unit. The intracorporeal unit may include a secondary coil that is electro-magnetically induced by the primary coil, a light receiving element that receives the electric stimulus signal from the light emitting element, a signal processing circuit that processes the electric stimulus signal received by the light receiving element, and a plurality of electrodes that transmits the electric stimulus signal processed by the signal processing circuit to the retina.

15 Claims, 12 Drawing Sheets

WINDOW EXTRACTION

FIG. 8(C)

QUANTIZATION

FIG. 8(A)

EYE-GAZE POINT

WINDOW (20°–30°)

FULL VISUAL FIELD OF CAMERA (60°–80°)

ARTIFICIAL EYE SYSTEM

TECHNICAL FIELD

The present invention relates to an artificial eye system.

BACKGROUND ART

Despite the recent advancement in medical technologies, an effective cure for blindness has not been devised yet. Blindness is not limited to a mere loss of a visual function but is a disease seriously affecting the patient's mental life and social life. Therefore, technologies for curing blindness are acutely demanded.

One of the blindness cure technologies is implemented in an artificial eye system designed to replace the function of a diseased part such as the retina or the optic nerve with an artificial entity. In general, the artificial eye system comprises an extracorporeal image receiving element and a nerve stimulating electrode implanted in an intracorporeal region. Image information received by the image receiving element is transmitted to the brain via the stimulating electrode. Therefore, at least an image information transmission system for transmitting the image information and a power supply system for supplying power to the electrode are needed.

However, the study of the artificial eye system has just started. Something, which is movable with a user (blind patient) and has the image information transmission system and the power supply system combined appropriately, has not yet been available.

The present invention has been made in view of the above circumstances and has an object to provide an artificial eye system which has excellent usability and is practically feasible.

DISCLOSURE OF INVENTION

In order to accomplish the above object, the present invention has the constituent features described below.

(1) According to one aspect, the present invention provides an artificial eye system in which stimulus signal producing means converts an image signal, which represents an image of an outside world received by an image receiving element, into an electric stimulus signal, and the electric stimulus signal is transmitted from an electrode attached to a retina, the system including: an extracorporeal unit which is mounted outside a user's body; and an intracorporeal unit which is mounted inside the user's body, the extracorporeal unit including a visor and a power supply unit which supplies electricity to the visor, the visor including a primary coil, the image receiving element, and a light emitting element which transmits the image signal from the image receiving element as an imaging signal, and the intracorporeal unit including: a secondary coil which is electromagnetically induced by the primary coil; a light receiving element which receives the imaging signal from the light emitting element; a signal processing circuit which processes the imaging signal received by the light receiving element; and an electrode unit which has a plurality of electrodes that transmits the electric stimulus signal, which is processed by the signal processing circuit, to the retina.

The "visor" is an object to be mounted on the face in the same manner as glasses are. The visor may have any shape.

The "light emitting element" is an element that transmits an image signal, for example, a light-emitting diode for emitting infrared, red, green, or blue radiation. Among them, the employment of the infrared light emitting diode (for example, from 800 nm to 1000 nm) has the merits described below. Namely, ① since a human body is little affected and the transmittance of infrared light is high, an artificial eye system that is more reliable can be provided. ② The artificial eye system can be put to practical use without being legally restricted by the Radio Law or the like. ③ The artificial eye system is basically effective within a range within which light passes. ④ The light emitting element and the light receiving element can be manufactured at a low cost and compactly.

The "image signal" means a signal representing an image received by the image receiving element. Moreover, the "electric stimulus signal" is an electric signal to be transmitted from the electrodes to the retina. The image signal is converted into the electric stimulus signal by the stimulus signal producing means. This stimulus signal producing means may be included in either the extracorporeal unit or the intracorporeal unit according to an overall circuitry. In this description, the "imaging signal" signifies either the image signal or the electric stimulus signal.

The stimulus signal producing means includes either hardware (for example, a dedicated circuit formed in a semiconductor device) or software (more particularly, a computer and software). However, the stimulus signal producing means performs a relatively large number of calculations and therefore consumes a large amount of power. Consequently, the stimulus signal producing means is preferably included in the extracorporeal unit. Moreover, if the stimulus signal producing means were included as hardware in the intracorporeal unit, there would be difficulty in designing it compactly. Since the intracorporeal unit should be designed as compactly as possible, the stimulus signal producing means should be incorporated in the extracorporeal unit.

The "retina" includes retinal photoreceptor cells, retinal bipolar cells, and retinal ganglion cells. Preferably, the electric signal is applied to the retinal bipolar cells or the retinal ganglion cells. Therefore, the electrodes are preferably disposed within the retina rather than being mounted on the retina.

According to the present invention set forth in (1), the artificial eye system can move together with a user (blind patient) and therefore offers excellent usability. Moreover, the image signal is transferred while being carried by light. When the eyelids are closed, an image disappears. Compared with a case where an electromagnetic induction device is used to transfer an image signal, vision is perceived with a natural feeling.

(2) In the artificial eye system set forth in (1), the outer diameter of the secondary coil ranges approximately 5 mm to approximately 12 mm.

In this description, the range "from approx. 5 mm to approx. 12 mm" defining the size of the intracorporeal unit is a range permissible by the average diameters of the crystalline capsule and the ciliary furrow respectively, that is, the average diameters of approx. 7 mm and approx. 10 mm. When the size of the intracorporeal unit ranges from approx. 5 mm to approx. 8 mm, it can be mounted in the crystalline capsule. Moreover, when the size of the intracorporeal unit ranges approx. 8 mm to approx. 12 mm, it can be mounted in the ciliary furrow.

According to the present invention set forth in (2), the secondary coil can be mounted in the ciliary furrow or the crystalline capsule. Therefore, compared with a case where the secondary coil is disposed on the equatorial plane of the eyeball, the primary coil and the secondary coil are located close to each other. This leads to an improvement in the efficiency of electromagnetic induction between the coils.

(3) In the artificial eye system set forth in (1), the signal processing circuit is integrated together with the electrodes on a substrate, and the outer diameters of the secondary coil and the light receiving element range from approx. 5 mm to approx. 12 mm.

The secondary coil and the light receiving element need not be integrated with each other. However, when the secondary coil and the light receiving element are integrated with each other, the ease of handling improves.

According to the present invention set forth in (3), the components other than the signal processing circuit and the electrodes, that is, the secondary coil and the light receiving element may be implanted in the ciliary furrow or the crystalline capsule. Consequently, compared with the case where the secondary coil and the light receiving element are disposed in the eyeball, an implantation can be achieved easily. Moreover, the damage to a user caused by the implantation is limited.

(4) In the artificial system set forth in (4), the outer diameters of the signal processing circuit, the secondary coil, and the light receiving element range from approx. 5 mm to approx. 12 mm.

The signal processing circuit, the secondary coil, and the light receiving element need not always be integrated with one another. However, when they are integrated with one another, the ease of handling improves.

According to the present invention set forth in (4), the components other than the electrodes, that is, the signal processing circuit, the secondary coil, and the light receiving element can be implanted in the ciliary furrow or the crystalline capsule. Therefore, compared with a case where the components are disposed in the eyeball, the implantation can be achieved easily. The damage to a user caused by the implantation is limited.

(5) According to another aspect, the present invention provides an artificial eye system in which stimulus signal producing means converts an image signal, which represents an image of an outside world received by an image receiving element, into an electric stimulus signal, and the electric stimulus signal is transmitted from an electrode attached to a retina, the system including: an extracorporeal unit which is mounted outside a user's body; and an intracorporeal unit which is mounted inside the user's body, the extracorporeal unit including a visor and a power supply unit which supplies electricity to the visor, the visor including a power transmitter which transmits power, the image receiving element, and an imaging signal transmitter which transmits the image signal from the image receiving element as an imaging signal, and the intracorporeal unit including: a power receiver which receives the power from the power transmitter; an imaging signal receiver which receives the imaging signal from the imaging signal transmitter; a signal processing circuit which processes the imaging signal received by the imaging signal receiver; an electrode unit which has a plurality of electrodes that transmits the electric stimulus signal processed by the signal processing circuit to the retina; and a power storage element which supplies the power to the electrodes and the signal processing circuit.

The "power transmitter" and the "power receiver" are a pair of units that transmits or receives power to or from the intracorporeal unit or the extracorporeal unit. The power transmitter and the power receiver are connected to each other according to, for example, a wired method in which power lines are directly joined (in this case, the power lines extending from the extracorporeal unit and the intracorporeal unit have connectors that are detachably attached to each other for better usability), or a wireless method in which a primary coil (incorporated in the extracorporeal unit) and a secondary coil (incorporated in the intracorporeal unit) are used to transmit power through electromagnetic induction. Needless to say, any other method those skilled in the art can utilize can be adopted.

The "imaging signal transmitter" and the "imaging signal receiver" are a pair of units that transmits or receives an image signal to or from the intracorporeal unit or the extracorporeal unit. The imaging signal transmitter and the imaging signal receiver are connected to each other according to, for example, a wired method in which signal lines are directly joined (in this case, the signal lines extending from the extracorporeal unit and the intracorporeal unit have connectors that are detachably attached to each other for better usability) or a wireless method in which a primary coil (incorporated in the extracorporeal unit) and a secondary coil (incorporated in the intracorporeal unit) are used to transmit a signal through electromagnetic induction. Incidentally, the signal lines employed in the wired method include electric lines and optical fibers. The wireless method adopts not only electromagnetic induction but also a light signal transmitting/receiving form.

The "power storage element" is a generic element capable of storing power, for example, a battery (a primary battery or a secondary battery) or a capacitor. Moreover, the weight of the power storage element ranges from approx. 0.5 g to approx. 2 g.

When a user wearing the artificial eye system moves his/her eyes, the secondary coils may tilt. Consequently, the efficiency in electromagnetic induction between the primary and secondary coils may deteriorate, and electromotive force induced in the secondary coil may diminish. According to the present invention set forth in (5), even in such a case, since power stored in the power storage element can be used, a stable image signal can be transmitted to the retina.

(6) According to another aspect, the present invention provides an artificial eye system in which stimulus signal producing means converts an image signal, which represents an image of an outside world received by an image receiving element, into an electric stimulus signal, and the electric stimulus signal is transmitted from an electrode attached to a retina, the system including: an extracorporeal unit which is mounted outside a user's body; and an intracorporeal unit which is mounted inside the user's body, the extracorporeal unit including a visor and a power supply unit which supplies electricity to the visor, the visor including a power transmitter which transmits power, the image receiving element, an imaging signal transmitter which transmits the image signal from the image receiving element as an imaging signal, and an eye-gaze point recognizing unit which recognizes an eye-gaze point, the intracorporeal unit including: a power receiver which receives the power from the power transmitter; an imaging signal receiver which receives the imaging signal from the imaging signal transmitter; a signal processing circuit which processes the imaging signal received by the imaging signal receiver to produce the electric stimulus signal for stimulating the retina; and an electrode unit which has a plurality of electrodes that transmits the imaging signal, which has been processed by the signal processing circuit, to the retina, and the electric stimulus signal representing information acquired in a direction of the eye-gaze point recognized by the eye-gaze point recognizing unit being transmitted from the electrodes to the retina.

The "eye-gaze point recognizing unit" recognizes the user's eye-gaze point. A concrete example is a unit that recognizes an eye-gaze point on the basis of the movement of reflected light of light irradiated to the cornea according to the fact that the radius of curvature of the cornea is smaller than those of the other parts of the eyeball (that is, the cornea projects more greatly than the other parts do). Another unit that recognizes an eye-gaze point and can be adopted utilizes the fact that the intensity of light reflected from the eye on the light receiving element or the imaging element included in the visor located in front of the eyes changes along with a change in the ratio of the iris and the pupil to the sclera caused by the motion of the eyeball. Otherwise, an electro-oculogram (EOG), a video oculogram (VOG), or a search coil may be used to recognize an eye-gaze point.

When it says that "the electric stimulus signal representing information acquired in a direction of the eye-gaze point is transmitted from the electrodes to the retina," it means that ① the image receiving element is driven based on a direction recognized by the eye-gaze point recognizing unit. Otherwise, it means that: ② a visual field (an image receiving visual field) covered by the image receiving element is set to be larger than a visual field (a transmitting visual field) whose image is transmitted from the electrodes to the retina; and the transmitting visual field is defined within the image receiving visual field according to the direction of the eye-gaze point.

According to the present invention set forth in (6), when a user moves his/her eye-gaze point, the user can sense an image in the direction of the eye-gaze point. This results in an artificial eye system offering excellent usability.

(7) In the artificial eye system set forth in (6), the image receiving visual field whose image is represented by the image signal produced by the image receiving element is set to be larger than the transmitting visual field whose image is transmitted from the electrodes to the retina, and an image of a portion of the image receiving visual field located in the direction of the eye-gaze point recognized by the eye-gaze point recognizing unit is transmitted as an image of the transmitting visual field to the electrodes.

A circuit for defining the transmitting visual field within the image receiving visual field may be incorporated in the extracorporeal unit or the intracorporeal unit.

According to the present invention set forth in (7), an electric stimulus signal representing information of the transmitting visual field smaller than the image receiving visual field is transmitted from the electrodes. According to one method ①, part of an image receiving signal is extracted as a signal representing the transmitting visual field, and the part of the image receiving signal representing the transmitting visual field is adopted as the electric stimulus signal. According to the other method ②, after the image receiving signal is adopted as a full electric stimulus signal, part of the image receiving signal representing the transmitting visual field is adopted as the electric stimulus signal.

According to the present invention set forth in (7), the component for changing images with the movement of an eye-gaze point is not hardware (for example, a component for driving the image receiving element) but software. This leads to a simplified overall configuration.

(8) In the artificial eye system set forth in (1) to (7), the electrode unit has a plurality of pores that penetrates through the electrode unit in a direction of a thickness.

The "pores" are holes that have the size permitting nutrition to pass through the electrode unit.

According to the present invention set forth in (8), since the plurality of pores is bored in the electrode unit, nutrition can be fed from the cells of the sclera to the cells of the retina. The electrode unit can therefore be implanted below the retina. Compared with a case where the electrode unit is mounted on the retina, the power of an output signal can be lowered. Consequently, even when the secondary coil is small and induced electromotive force is limited, an excellent image signal can be transmitted.

BRIEF DESCRIPTION OF THE DRAWINGS

FIG. 5 shows the whole of an intracorporeal unit, (A) is a plan view, and (B) is a cutaway side view of a secondary coil;

FIG. 8 shows the relationship between an image receiving visual field and a transmitting visual field, (A) shows the image receiving visual field, (B) shows the transmitting visual field, and (C) shows an image actually transmitted to electrodes;

BEST MODE FOR CARRYING OUT THE INVENTION

Next, embodiments of the present invention will be described below. The technological scope of the present invention is not limited to the embodiments. Various application of the invention can be implemented without departing from the scope of the invention. Moreover, the technological scope of the invention encompasses an equivalent scope.

Referring to FIG. 1 to FIG. 10, an embodiment of the present invention will be described below.

Figure 1:
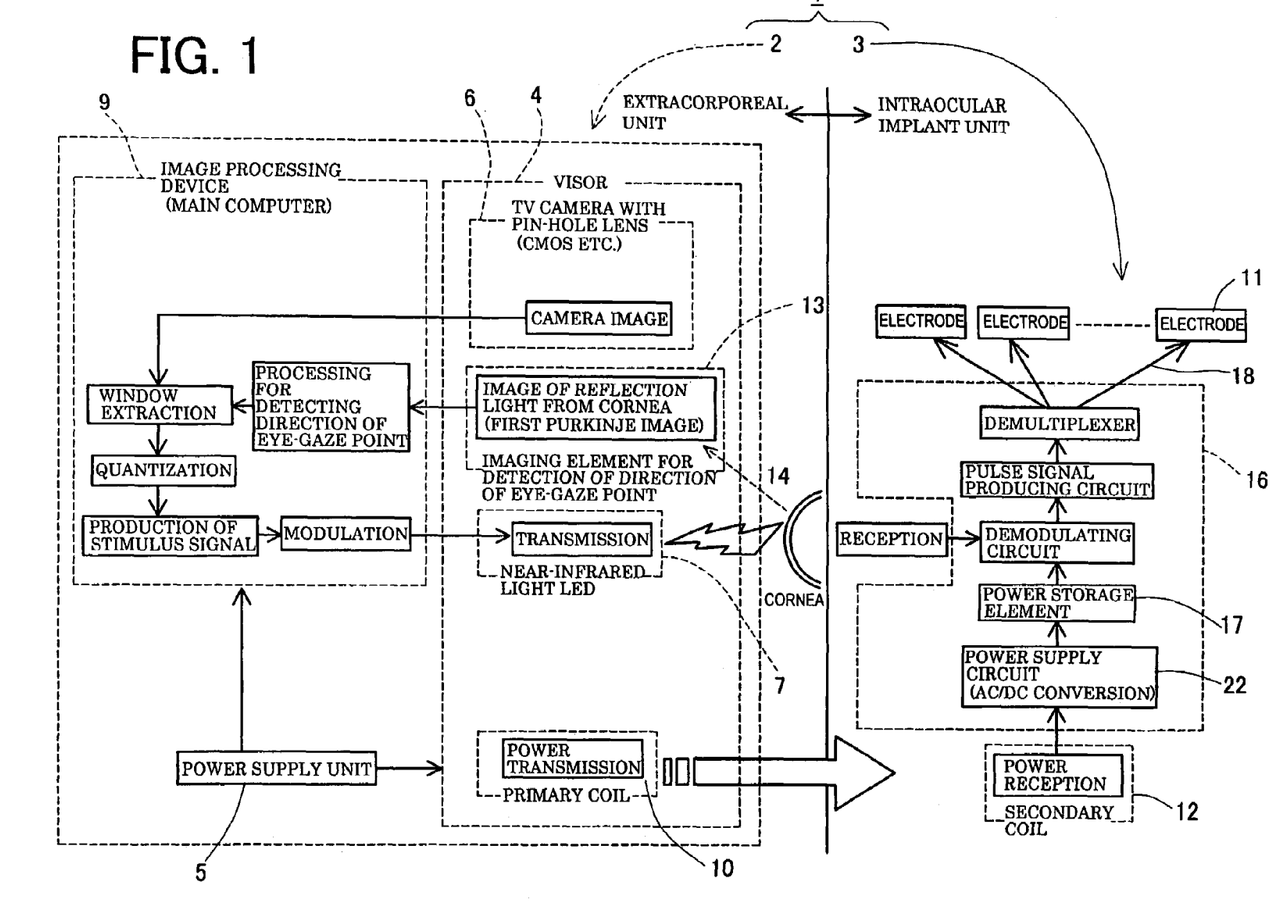
FIG. 1 shows the overall configuration of an artificial eye system according to a present embodiment.

As shown in FIG. 1, an artificial eye system 1 in the present embodiment is constructed of an extracorporeal unit 2 which is mounted outside a user's body and an intracorporeal unit 3 which is mounted inside the user's body (specifically, in the eyeball).

The operation of the artificial eye system 1 will first briefly be explained below. A visor 4 included in the extracorporeal unit 2 has a TV camera 6 and eye-gaze point recognizing units 13. A signal component of a signal received by the TV camera 6 which represents information of a direction recognized by the eye-gaze point recognizing units 13 is extracted by a computer 9, whereby a transmission signal is produced. The signal is transmitted to the intracorporeal unit 3 via light emitting devices 7, and then processed appropriately. The resultant signals are then transmitted to electrodes 11 implanted in a region near the retina. Thus, each electric signal is applied to the remaining retinal bipolar cells or retinal ganglion cells (hereinafter, simply, the retina). Moreover, the extracorporeal unit 2 includes a power supply unit 5 that drives the computer 9. Primary coils 10 and secondary coils 12 are incorporated in the extracorporeal unit 2 and the intracorporeal unit 3 respectively. Power is transmitted to the intracorporeal unit 3 owing to electromagnetic induction occurring between each pair of the coils 10 and the coils 12.

Figure 2:
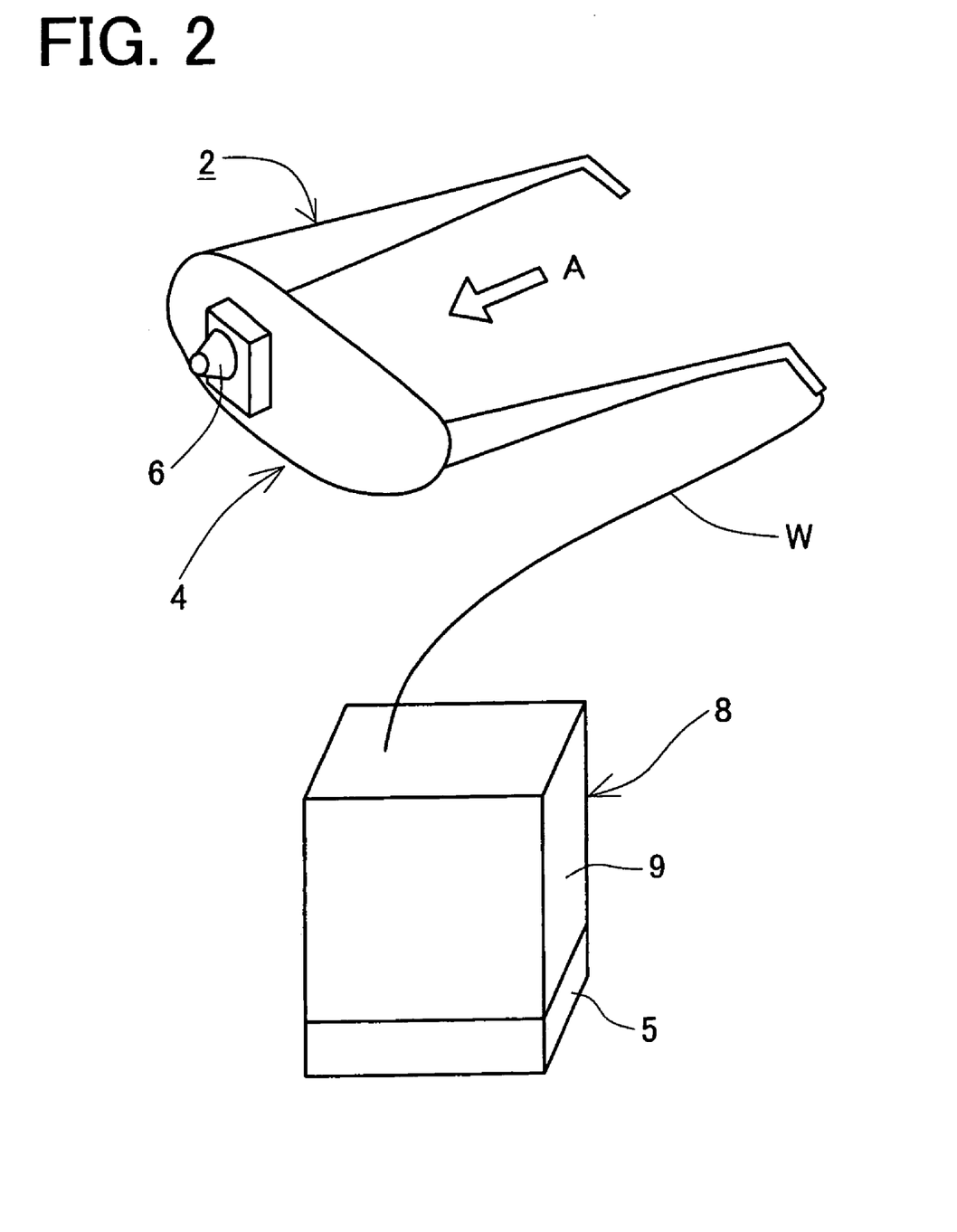
FIG. 2 is a perspective view schematically showing a whole extracorporeal unit included in the artificial eye system.

Next, the components will be detailed below. FIG. 2 schematically shows the whole extracorporeal unit 2. The extracorporeal unit 2 falls broadly into the visor 4 which a user wears in front of his/her eyes, and a processing unit 8 that includes the power supply unit 5 for supplying power to the visor 4. These members 4 and 8 are connected to each other through a wire W whereby electricity and signals are transferred. At an upper part of the processing unit 8, the computer 9 is located for supplying electricity, processing image data, and transmitting a signal. The power supply unit 5 (secondary battery) is located under the computer 9.

Figure 3:
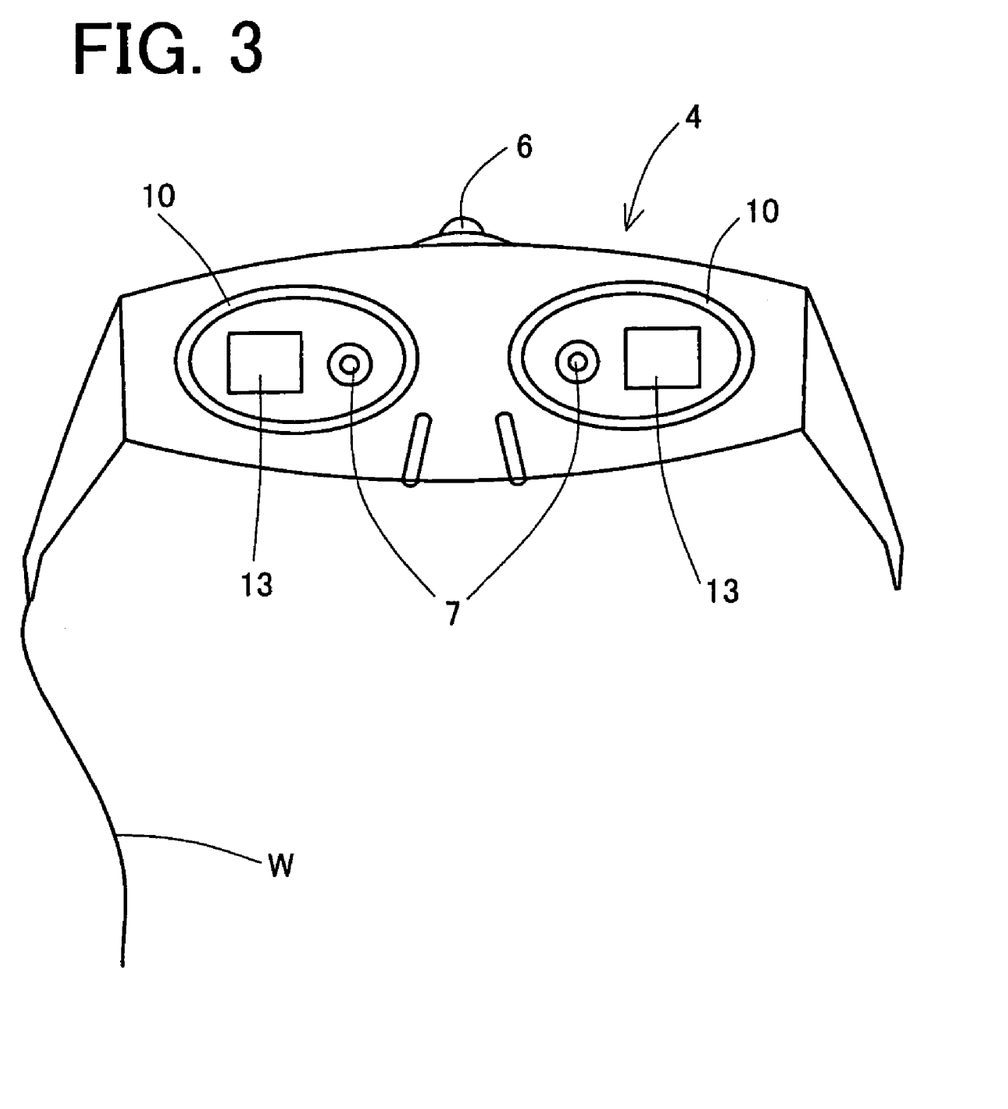
FIG. 3 shows a visor seen in the direction of arrow A in FIG. 1.

Moreover, the visor 4 includes the TV camera 6 serving as an image receiving element for receiving a picture image of an outside world, and the light emitting element 7 for transmitting an image signal sent from the TV camera 6 into the intracorporeal unit 2 (see FIG. 2 as well as FIG. 3). In the present embodiment, a near infrared light emitting diode is adopted as the light emitting element 7. As shown in FIG. 3, the primary coils 10 and the eye-gaze point recognizing units 13 are provided on the back surface of the visor 4 (at two positions facing the user's eyes). The primary coils 10 are electromagnetically coupled to the secondary coils 12 included in the intracorporeal unit 3 that will be described later.

In the present embodiment, a single TV camera 6 is provided in the visor 4. The present invention is not limited thereto. Alternatively, two TV cameras may be arranged for the right and left eyes.

Figure 4:
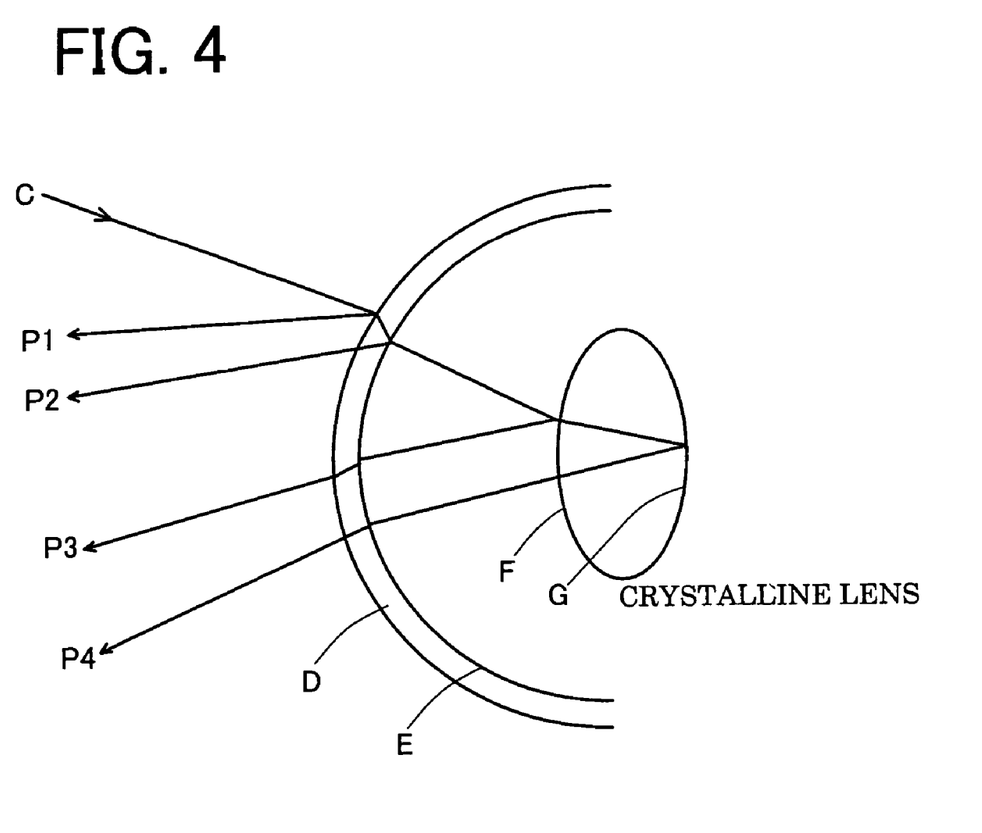
FIG. 4 shows the operation of an eye-gaze point recognizing unit.

Moreover, the eye-gaze point recognizing unit 13 includes a light receiving element that detects light emitted from the light emitting element 7 and reflected from the eyeball. As shown in FIG. 4, incident light C emitted from the light emitting element 7 is reflected from each of the surface D of the cornea, the bottom E of the cornea, the surface F of the crystalline lens, and the bottom G of the crystalline lens (P1 to P4 in FIG. 4 denote light rays reflected from the surfaces and bottoms D to G). In the present embodiment, the light receiving element receives the light reflected from the surface D of the cornea (P1, a first Purkinje image). The direction of the eye-gaze point is recognized based on the incident light C and reflected light P1.

Figure 5A:
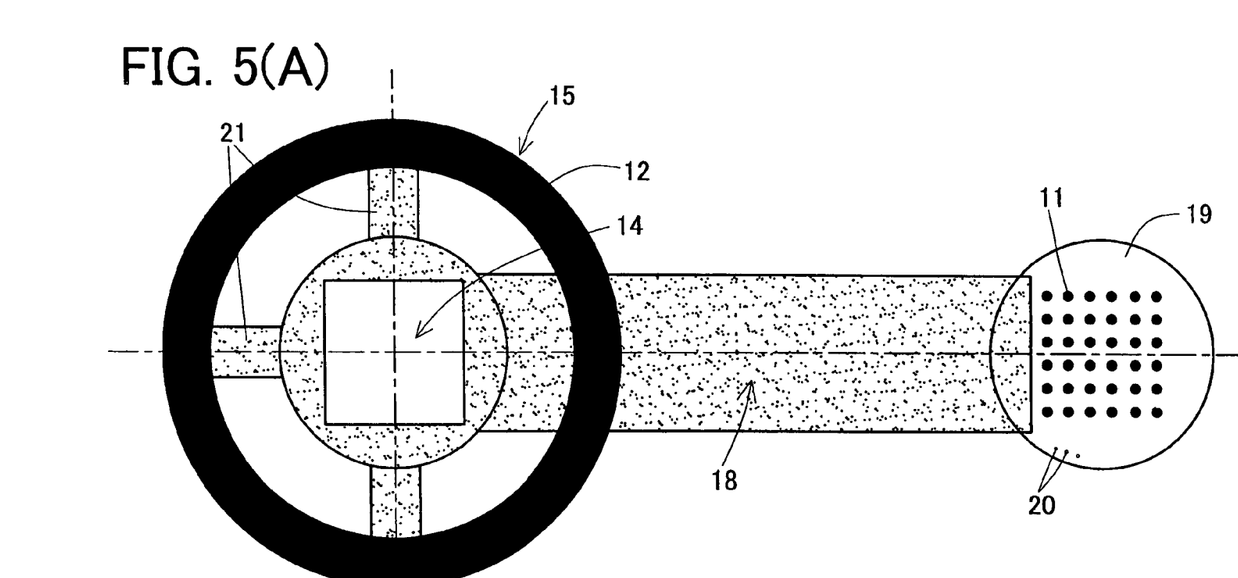
Figure 5B:
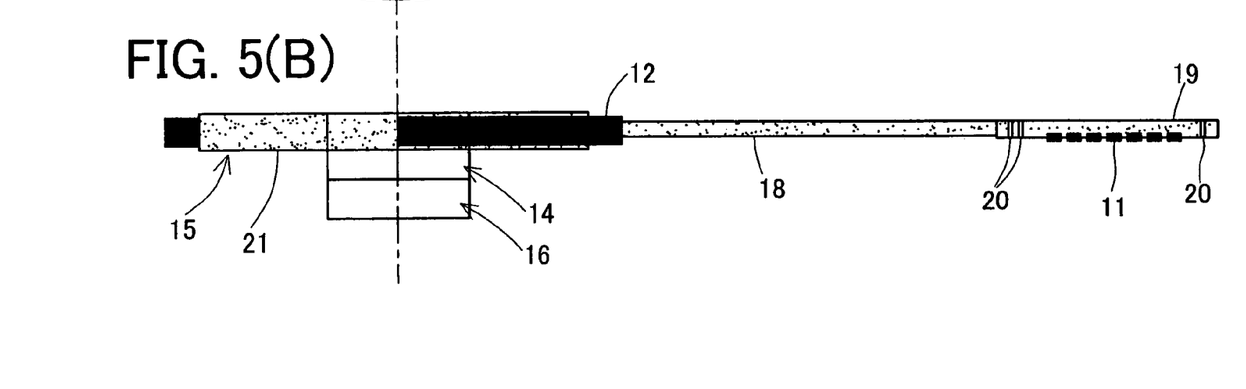

The configuration of the intracorporeal unit 3 will be described below, referring to FIG. 5. The intracorporeal unit 3 includes a front unit 15 which is implanted in the anterior part of the eyeball, and an electrode unit 19 composed of a plurality of electrodes 11 that transmits an electric signal to the retina N. The members 15 and 19 are connected through a cable 18. The front unit 15 includes the secondary coil 12 that receives the power from the primary coil 10, the light receiving element 14 that receives the image signal from the light emitting element 7, and an integrated circuit 16 provided with a signal processing circuit which processes the image signal received by the light receiving element 14, and a demultiplexer. The light receiving element 14 and the integrated circuit 16 have substantially the same outer diameter. The secondary coil 12 has an outer diameter larger than the outer diameters of the light receiving element 14 and the integrated circuit 16. The outer diameter of the secondary coil 12 ranges approx. 5 mm to approx. 8 mm, and is equal to or slightly larger than the inner diameter of an opening of the crystalline capsule H. Moreover, the light receiving element 14 and the integrated circuit 16 are concentrically integrated with each other on the back of the secondary coil 12 via a resin substrate 21.

In the present embodiment, the light receiving element 14 and the integrated circuit 16 are concentrically integrated with each other on the back of the secondary coil 12 via the resin substrate 21; but the present invention is not limited thereto as long as the light receiving element 14 and the secondary coil 12 can be placed in the anterior part of the eye and integrated into the resin substrate 21. For example, the integrated circuit 16 may be set on the back of the electrode unit 19. Moreover, the light receiving element 14 and the integrated circuit 16 may be placed on the same side as the side of the substrate 21 on which the secondary coils 12 are placed. Moreover, the light receiving element 14 and the integrated circuit 16 may not always be concentric to the secondary coil 12. Furthermore, although the light receiving element 14 and the integrated circuit 16 are separate elements in the present embodiment, the present invention is not limited to this mode. Alternatively, the light receiving element 14 and the integrated circuit 16 may be integrated with each other.

Moreover, the integrated circuit 16 includes a power supply circuit 22 that converts an alternating current caused to flow by the secondary coil 12 into a direct current, and a power storage element 17 in which power is stored when power is abundant. The front unit 15 and the electrodes 11 are connected to one another through the cable 18.

The electrode unit 19 is formed of a thin polymer member having appropriate elasticity and being shaped substantially like a disk. The plurality of electrodes 11 for transmitting an electric signal to the retina N is arranged in rows and columns, or in a matrix pattern, with a predetermined space between adjoining electrodes. The electrode unit 19 has a plurality of pores 20 formed penetrating through the electrode unit 19 in the direction of the thickness (for example, a laser may be used to bore the pores or a porous polymer may be adopted). Consequently, nutrition can pass through the electrode unit 19 (for brevity's sake, part of the pores 20 alone is shown in FIG. 5). Moreover, when a polymer member having numerous apertures but not the through holes is employed, after the electrode unit 19 is placed on or under the retina N, peripheral cells are expected to grow while invading into the apertures. The degree of adhesion between the electrode unit 16 and retina N is expected to improve owing to the growth of the peripheral cells.

Figure 6:
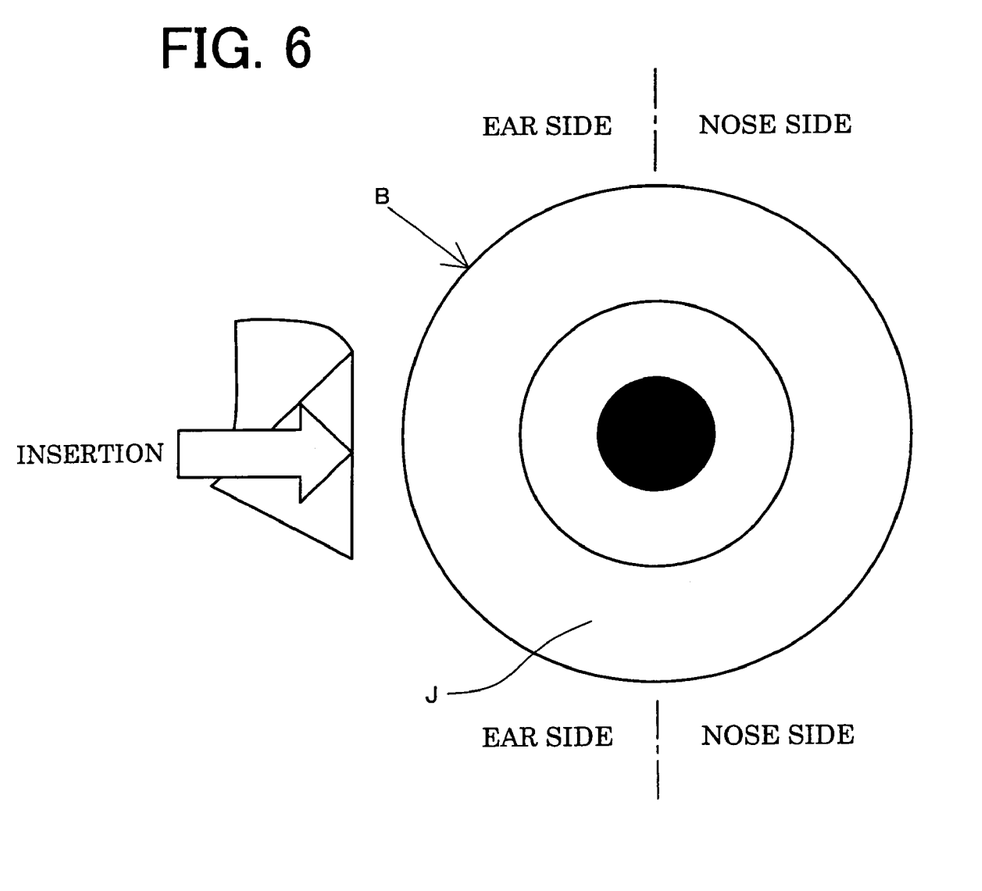
FIG. 6 shows a state before the intracorporeal unit is implanted in an eyeball.
Figure 7:
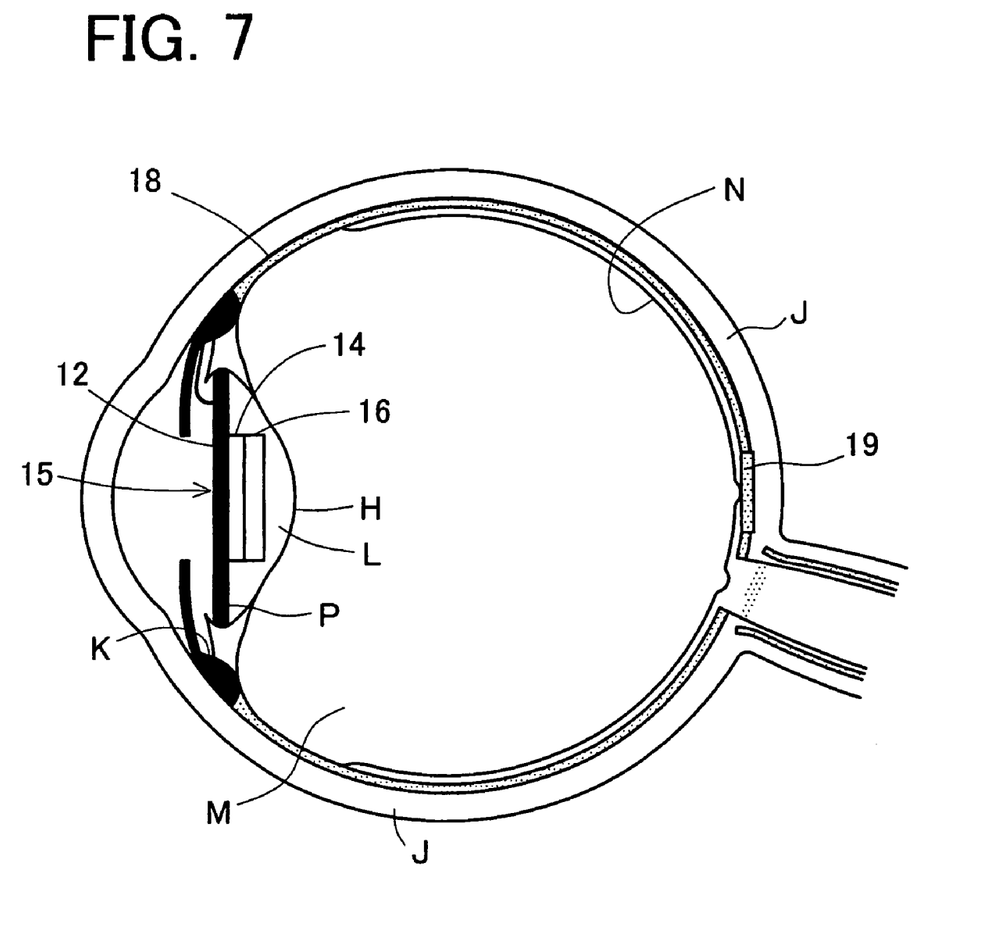
FIG. 7 is a side sectional view showing the eyeball in which the intracorporeal unit has been implanted.

In order to implant the intracorporeal unit 3 in the eyes, as shown in FIG. 6, the sclera J of each eye in a region approx. 1.5 mm away from the corneal annular margin B on the side of the cornea near the ear is resected by a length ranging from 7 mm to 8 mm. Thus, an insertion port is created. The front unit 15, the electrode unit 19, and the cable 18 are inserted into the eye through the insertion port. Moreover, after the crystalline lens is taken out, the front unit 15 is implanted so that the external periphery of the second coil 12 will be held with the muscle on the perimeter P of the opening of the crystalline capsule H. Moreover, the cable 18 is implanted while being laid on the internal surface of the sclera J, and the electrode unit 19 is placed inside the retina N.

Next, referring mainly to FIG. 8 to FIG. 10, the operation and effect of the present embodiment having the foregoing components will be described below.

Figure 8A:
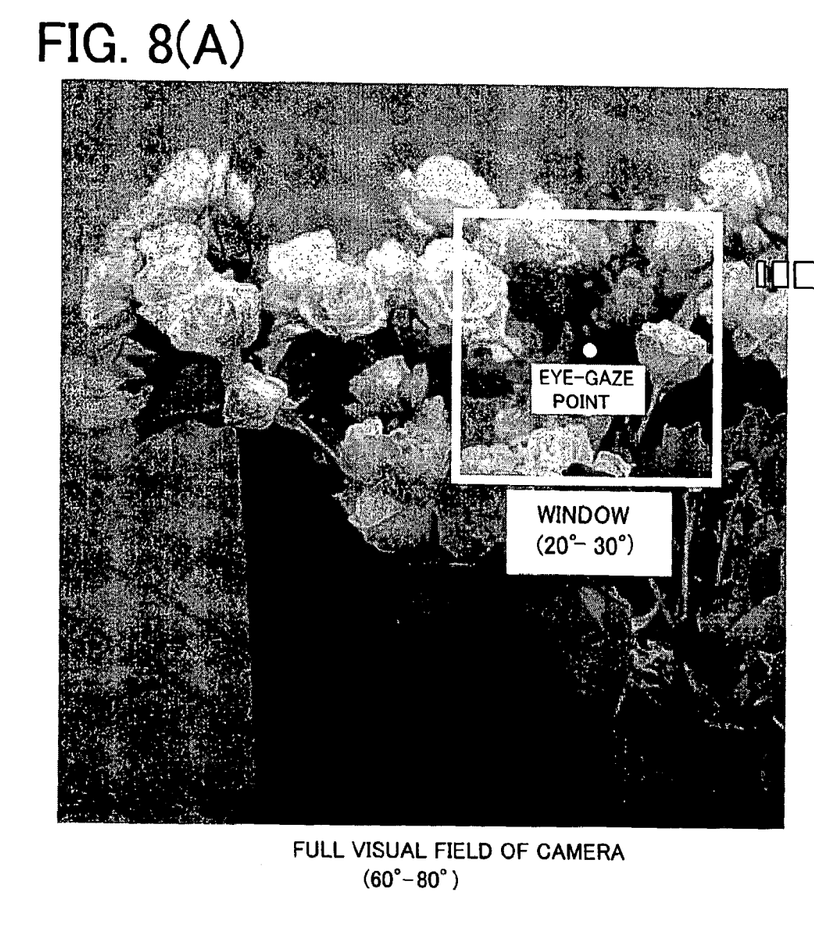

Image information processing will first be summarized. The TV camera 6 includes, for example, approx. one million pixel locations. An image receiving visual field (that is, an area whose information is represented by an image signal produced by the TV camera 6) whose image is received by the TV camera 6 is a range defined with an angle ranging, as shown in FIG. 8(A), from approx. 60° to approx. 80°. Incidentally, the number of electrodes 11 for transmitting an electric signal to the retina N ranges from about several tens of electrodes to several thousands of electrodes at most according to the current technological level. Almost all of image information received by the TV camera 6 is therefore not transmitted to the retina N. In the present embodiment, accordingly, the image receiving visual field of the TV camera 6 (FIG. 8(A)) is set to be larger than the transmitting visual field (FIG. 8(B)) whose image is transmitted from the electrodes 11 to the retina N. A window (transmission visual field) is defined in the image receiving visual field according to the direction of the eye-gaze point recognized by the eye-gaze point recognizing unit 13. An image signal representing the image of the window is quantized (FIG. 8(C)), and transmitted from the electrodes 11 to the retina N.

In the present embodiment, the image receiving visual field whose image is received by the TV camera 6 is a range defined with an angle ranging from approx. 60° to approx. 80°. The present invention is not limited to this mode. Alternatively, a range defined with an angle ranging, for example, from 60° to 180° will do.

Next, referring to FIG. 9, image signal processing to be performed in the extracorporeal unit 2 will be described below.

Figure 9:
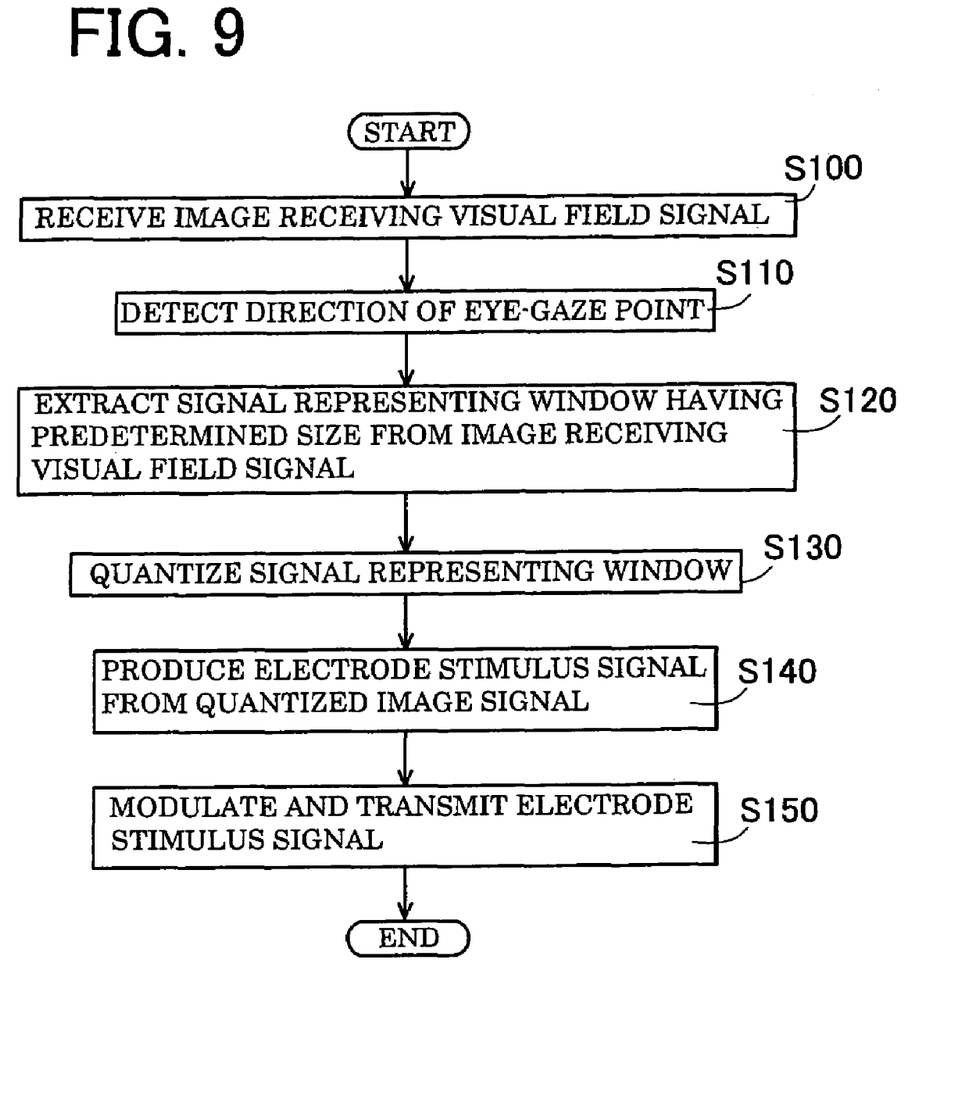
FIG. 9 is a flowchart describing image signal processing to be performed in the extracorporeal unit.
Figure 10:
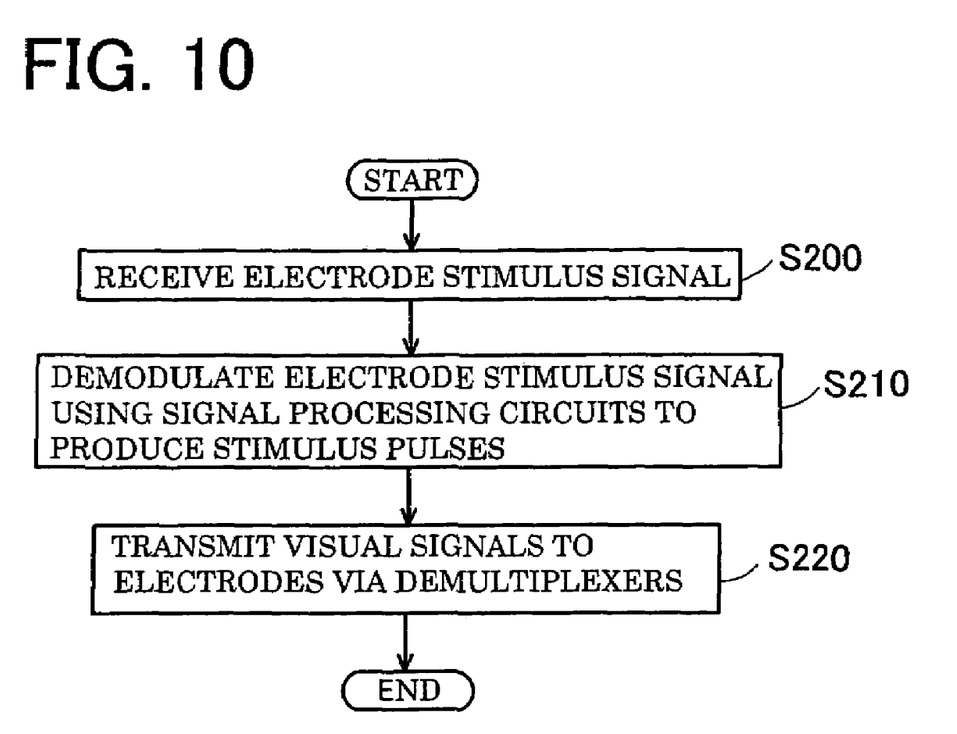
FIG. 10 is a flowchart describing imaging signal processing to be performed in the intracorporeal unit.

The TV camera 6 included in the visor 4 receives an image of a forward image receiving visual field (S100 in FIG. 9; FIG. 8(A)).

Figure 8B:
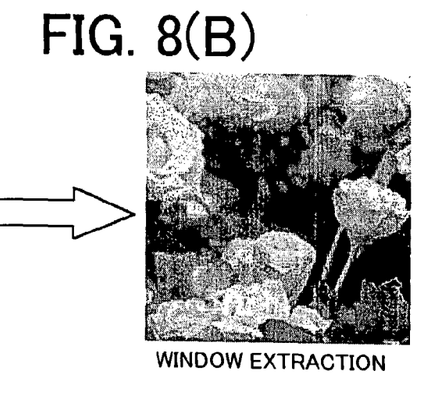
Figure 8C:
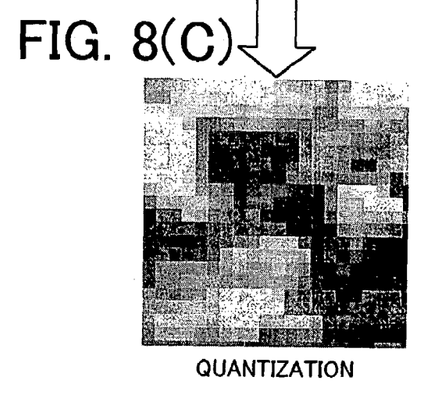

On the other hand, the eye-gaze point recognizing units 13 and computer 9 detect the direction of a user's eye-gaze point (S110). An image signal representing an image of a window having a predetermined size in the direction of the eye-gaze point is extracted from an image signal representing the image of the whole image receiving visual field (S120; FIG. 8(B)). The image signal representing the image of the window represents a large amount of information for the number of electrodes 11. Therefore, the image signal representing the image of the window is quantized in order to produce a signal suitable for the number of electrodes 11 (S130).

Thereafter, stimulus signal producing software is used to produce an electrode stimulus signal from the quantized image signal (S140). Furthermore, the electrode stimulus signal is modulated and transmitted from the light emitting elements 7 (S150). For the modulation of the electrode stimulus signal, for example, a pulse frequency, a pulse width, a pulse amplitude, and the number of pulses can be used as parameters for modulation.

Next, referring to FIG. 10, image signal processing to be performed in the intracorporeal unit 3 will be described. First, the light receiving elements 14 receives the electrode stimulus signal from the light emitting elements 7 (S200). Thereafter, the signal processing circuits included in the integrated circuit 16 demodulate the respective electric stimulus signals so as to produce pulse signals for stimulating the electrodes 11 (S210).

Next, the pulse signals are transmitted to the electrodes 11 via the demultiplexers (S220). With the pulse signals sent from the electrodes 11, electric signals are applied to the remaining retinas N of the eyes.

As mentioned above, according to the present embodiment, the artificial eye system 1 is movable together with a user and therefore provides excellent usability. Moreover, the image signal is transmitted via the light emitting elements 7 and light receiving elements 14 while being carried by light. Therefore, when the eyelids are closed, an image disappears. Consequently, compared with a case where an image signal is transferred using an electromagnetic induction device, vision can be perceived with a natural feeling.

Moreover, the secondary coil 12 can be mounted in the ciliary furrow K or the crystalline capsule H. Compared with a case where the secondary coil 12 is placed on the equatorial plane of the eyeball M, the primary coil 10 and the secondary coil 12 are located close to each other. The efficiency in electromagnetic induction between the coils 10 and 12 can be improved.

Moreover, the components other than the electrodes 11, that is, the integrated circuit 16 including the signal processing circuit, the secondary coil 12, and the light receiving element 14 are mounted on and integrated to the same substrate, and formed to have an appropriate size. Therefore, the components can be implanted in the ciliary furrow K or the crystalline capsule H. Consequently, compared with a case where the components are placed on the eyeball M, the implantation is easy to do. The damage to a user caused by the implantation is limited.

When a user wearing the artificial eye system 1 moves his/her eyeballs, the secondary coils 12 may tilt. Consequently, the efficiency in electromagnetic induction between each pair of the primary coils 10 and the secondary coils 12 may deteriorate, and electromotive force induced in the secondary coil 12 may decrease. Even in this case, since power in the power storage element 17 can be used, a stable image signal can be transmitted to the retina N.

Moreover, the power storage element 17 can be implanted in the ciliary furrow K or the crystalline capsule H. Therefore, compared with a case where the power storage element is placed on the eyeball M, the implantation is easy to do. The damage to a user caused by the implantation is limited.

Moreover, since the electrode unit 19 has a plurality of pores 20, nutrition can be supplied from the cells of the sclera J to the cells of the retina N. Therefore, the electrode unit can be implanted under the retina. Compared with a case where the electrode unit is mounted on the retina, the power of a signal to be transmitted to the retina N can be lowered. Consequently, even when the secondary coil 12 is small and induced electromotive force is limited, a satisfactory electric stimulus signal can be transmitted to the retina N.

Moreover, the eye-gaze point recognizing units 13 are provided so that an image acquired in the direction of the eye-gaze point recognized by these units 13 is transmitted to the retina N, which achieves the artificial eye system 1 with excellent usability.

Moreover, the component for changing images with the movement of the eye-gaze point is not hardware (for example, not a component for driving a light receiving element) but software. This results in a simple overall configuration.

OTHER EMBODIMENT

Figure 11:
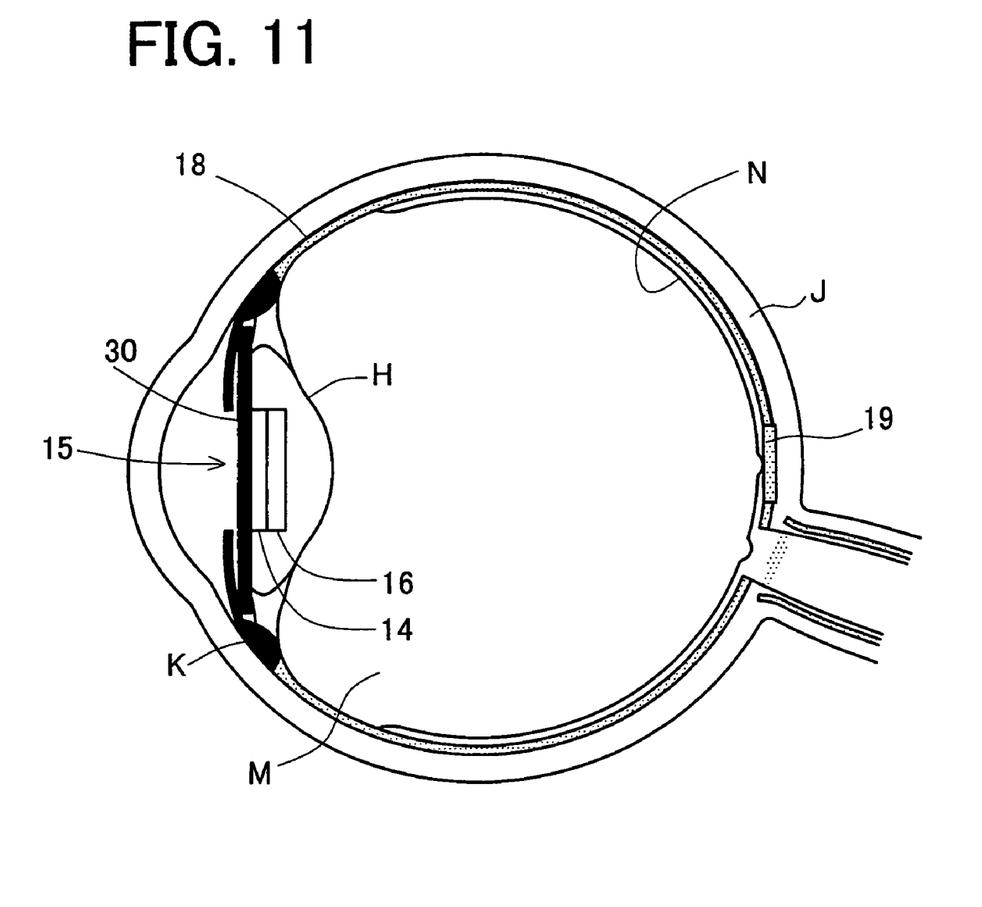
FIG. 11 is a side sectional view showing a front device mounted in the ciliary furrow according to another embodiment.
Figure 12:
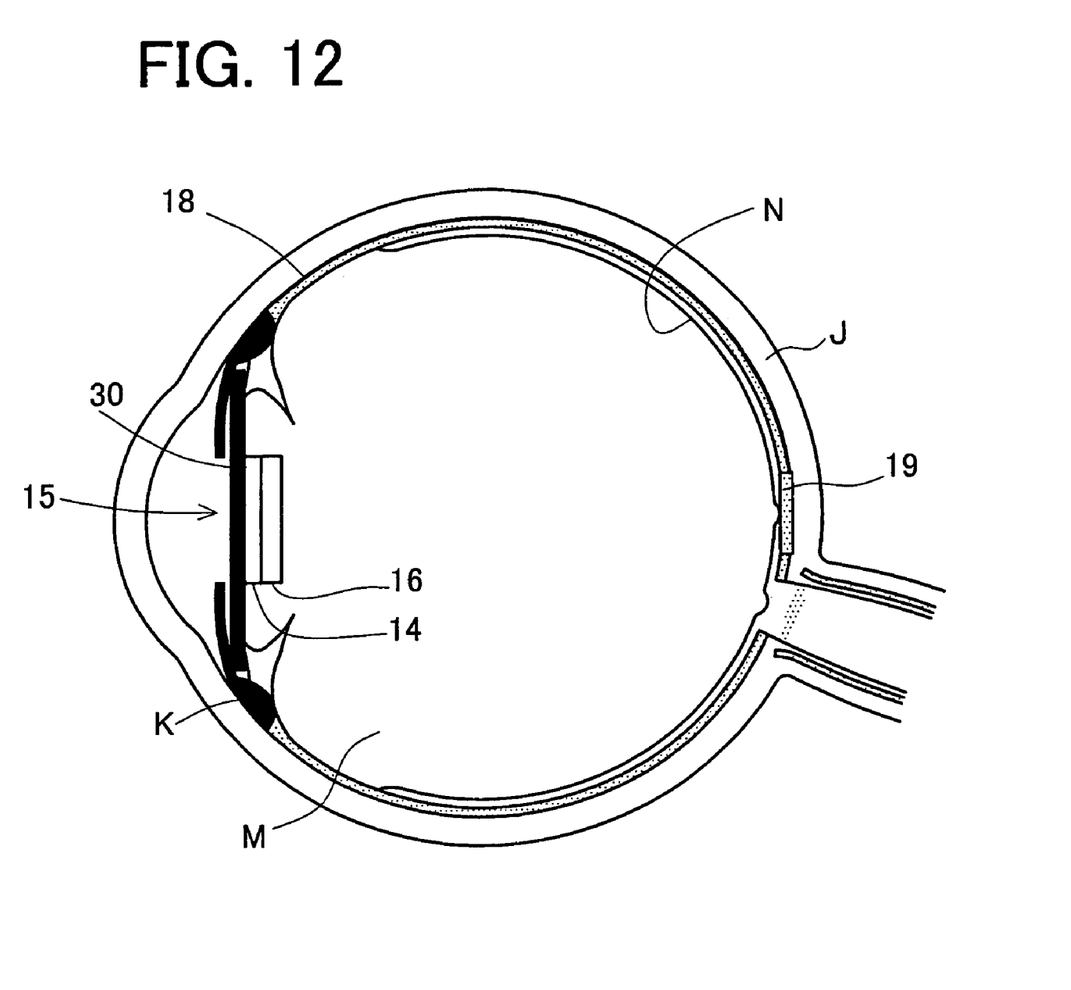
FIG. 12 is a side sectional view showing the front device mounted in the ciliary furrow according to another embodiment.

Next, referring to FIG. 11, other embodiment will be described. The same reference numerals will be assigned to components identical to those of the above embodiment, and the description of those components are omitted. In this embodiment, the outer diameter of a secondary coil 30 is determined to be approx. 11 mm. The secondary coil 30 is placed in the ciliary furrow K. According to the present embodiment, the outer diameter of the secondary coil 30 is larger than that of the secondary coil 12, which leads to the improvement in the efficiency of electromagnetic induction. Depending on a user, his/her lens and crystalline capsule H may be entirely enucleated. In this case, as shown in FIG. 12, the secondary coil 30 is mounted in (stitched to) the ciliary furrow K. Since the outer diameter of the secondary coil 30 ranges from approx. 8 mm to approx. 12 mm (more preferably, from approx. 9 mm to approx. 11 mm), the intracorporeal unit 3 can be mounted in a person who has the crystalline lens and the crystalline capsule H of one eye enucleated.

INDUSTRIAL APPLICABILITY

As described above, according to the present invention, there is provided an artificial eye system which has excellent usability and is practically feasible.

The invention claimed is:

1. An artificial eye system in which stimulus signal producing means converts an image signal, which represents an image of an outside world received by an image receiving element, into an electric stimulus signal, and the electric stimulus signal is transmitted from an electrode attached to a retina, the system including:
   an extracorporeal unit which is mounted outside a user's body; and
   an intracorporeal unit which is mounted inside the user's body,
   wherein the extracorporeal unit includes a visor and a power supply unit which supplies electricity to the visor,
   the visor includes a primary coil, the image receiving element, and a light emitting element which transmits the image signal from the image receiving element as an imaging signal, and
   the intracorporeal unit includes: a secondary coil which is electro-magnetically induced by the primary coil to supply electric power to the intracorporeal unit; a single light receiving element which receives the imaging signal from the light emitting element; a signal processing circuit which processes the imaging signal received by the light receiving element; and an electrode unit which is placed away from the signal processing circuit and electrically connected to the signal processing circuit though a cable, and has a plurality of electrodes that transmits the electric stimulus signal to the retina and a demultiplexer that transmits the electric stimulus signal processed by the signal processing circuit to each electrode.

2. The artificial eye system according to claim 1, wherein an outer diameter of the secondary coil ranges approximately 5 mm to approximately 12 mm.

3. The artificial eye system according to claim 2, wherein the signal processing circuit is integrated together with the electrodes on a substrate, and the outer diameters of the secondary coil and the light receiving element range from approx. 5 mm to approx. 12 mm.

4. The artificial eye system according to claim 2, wherein the electrode unit has a plurality of pores formed penetrating through the electrode unit in a direction of a thickness.

5. The artificial eye system according to claim 1, wherein the signal processing circuit is integrated together with the electrodes on a substrate, and the outer diameters of the secondary coil and the light receiving element range from approx. 5 mm to approx. 12 mm.

6. The artificial eye system according to claim 5, wherein the electrode unit has a plurality of pores formed penetrating through the electrode unit in a direction of a thickness.

7. The artificial eye system according to claim 1, wherein the outer diameters of the signal processing circuit, the secondary coil, and the light receiving element range from approx. 5 mm to approx. 12 mm.

8. The artificial eye system according to claim 7, wherein the electrode unit has a plurality of pores formed penetrating through the electrode unit in a direction of a thickness.

9. The artificial eye system according to claim 1, wherein the electrode unit has a plurality of pores formed penetrating through the electrode unit in a direction of a thickness.

10. An artificial eye system in which stimulus signal producing means converts an image signal, which represents an image of an outside world received by an image receiving element, into an electric stimulus signal, and the electric stimulus signal is transmitted from an electrode attached to a retina, the system including:
    an extracorporeal unit which is mounted outside a user's body; and
    an intracorporeal unit which is mounted inside the user's body,
    wherein the extracorporeal unit includes a visor and a power supply unit which supplies electricity to the visor,
    the visor includes a power transmitter which transmits power by electromagnetic induction, the image receiving element, and an imaging signal transmitter which transmits the image signal from the image receiving element as an imaging signal, and
    the intracorporeal unit includes: a power receiver which receives the power from the power transmitter by electromagnetic induction; a single imaging signal receiver which receives the imaging signal from the imaging signal transmitter; a signal processing circuit which processes the imaging signal received by the imaging signal receiver; an electrode unit which is placed away from the signal processing circuit and electrically connected to the signal processing circuit through a cable, and has a plurality of electrodes that transmits the electric stimulus signal to the retina and a demultiplexer that transmits the electric stimulus signal processed by the signal processing circuit to each electrode; and a power storage element which supplies the power to the electrodes and the signal processing circuit.

11. The artificial eye system according to claim 10, wherein the electrode unit has a plurality of pores formed penetrating through the electrode unit in a direction of a thickness.

12. An artificial eye system in which stimulus signal producing means converts an image signal, which represents an image of an outside world received by an image receiving element, into an electric stimulus signal, and the electric stimulus signal is transmitted from an electrode attached to a retina, the system including:
    an extracorporeal unit which is mounted outside a user's body; and an intracorporeal unit which is mounted inside the user's body, wherein the extracorporeal unit includes a visor and a power supply unit which supplies electricity to the visor, the visor includes a power transmitter which transmits power by electromagnetic induction, the image receiving element, an imaging signal transmitter which transmits the image signal from the image receiving element as an imaging signal, and an eye-gaze point recognizing unit which recognizes an eye-gaze point, the intracorporeal unit includes: a power receiver which receives the power from the power transmitter by electromagnetic induction; a single imaging signal receiver which receives the imaging signal from the imaging signal transmitter; a signal processing circuit which processes the imaging signal received by the imaging signal receiver to produce the electric stimulus signal for stimulating the retina; and an electrode unit which is placed away from the signal processing circuit and electrically connected to the signal processing circuit through a cable, and has a plurality of electrodes that transmits the electric stimulus signal to the retina and a demultiplexer that transmits the electric stimulus signal processed by the signal processing circuit to each electrode, and the electric stimulus signal representing information acquired in a direction of the eye-gaze point recognized by the eye-gaze point recognizing unit being transmitted from the electrodes to the retina.

13. The artificial eye system according to claim 12, wherein an image receiving visual field whose image is represented by the image signal produced by the image receiving element is set to be larger than a transmitting visual field whose image is transmitted from the electrodes to the retina, and an image of a portion of the image receiving visual field located in the direction of the eye-gaze point recognized by the eye-gaze point recognizing unit is transmitted as an image of the transmitting visual field to the electrodes.

14. The artificial eye system according to claim 13, wherein the electrode unit has a plurality of pores formed penetrating through the electrode unit in a direction of a thickness.

15. The artificial eye system according to claim 12, wherein the electrode unit has a plurality of pores formed penetrating through the electrode unit in a direction of a thickness.

* * * * *